Figure 1:

United States Patent [19]
Sills et al.

[11] Patent Number: 4,565,721
[45] Date of Patent: Jan. 21, 1986

[54] CARBOWAX STICKS FOR PREPARATION OF THE CARBOWAX FIXATIVE USE IN CANCER CYTOLOGY

[76] Inventors: Kenneth Sills; Bernard Sills, both of 535 Cathedral Pkwy., New York, N.Y. 10025

[21] Appl. No.: 379,313

[22] Filed: May 18, 1982

[51] Int. Cl.⁴ ............................................... B32B 9/04
[52] U.S. Cl. ...................................... 428/36; 206/529; 424/DIG. 15; 424/DIG. 5; 428/375; 428/484; 428/500
[58] Field of Search .......................... 206/529; 604/288; 428/375, 36, 35, 500, 484; 424/DIG. 15, DIG. 5

[56] References Cited

U.S. PATENT DOCUMENTS

| | | | |
|---|---|---|---|
| 2,523,683 | 9/1950 | DeMario | 424/DIG. 5 |
| 2,975,099 | 3/1961 | Goyan | 424/DIG. 15 |
| 3,163,576 | 12/1964 | Havemeyer | 424/DIG. 15 |
| 3,415,249 | 12/1968 | Sperti | 424/DIG. 15 |
| 4,252,789 | 2/1981 | Broad | 424/DIG. 5 |

OTHER PUBLICATIONS

ACTA Cytologica, "A Note on the History of Carbowax in Cytology", vol. 27, No. 2, Mar.-Apr. 1983, p. 204.

Primary Examiner—Edith Buffalow

[57] ABSTRACT

Carbowax PEG 1450 is the essential ingredient needed in preparing the alcoholic fixative now commonly used in cancer cytology. A new method is described showing how carbowax PEG 1450 sticks of uniform weight and length can be manufactured in thin polyethylene molds. The mold which is easily cut thru with a razor blade is left on to protect the wax stick until it is used. From these sticks any desired smaller weight of carbowax PEG 1450 can be calculated from markings stamped on the mold surface, from measurements on an English or metric straight ruler, or from an algebraic line graph or conversion table supplied with the molded stick. The vertical axis of the graph can be used for making measurements in either centimeters or inches. Thus it is no longer necessary to weigh out the small quantity of carbowax PEG 1450 needed to prepare the usual small volume of fixative needed for every day office or clinic use. Suggestions are given showing how the carbowax PEG 1450 fixative can be used.

7 Claims, 2 Drawing Figures

CARBOWAX STICKS FOR PREPARATION OF THE CARBOWAX FIXATIVE USE IN CANCER CYTOLOGY

Carbowax PEG 1450 added to any alcohol forms a unique fixative that is used extensively in the study of Cancer Cytology. In 1957 I described the original method for fixation and preservation of cytological smears using the solid carbowax PEG 1450 dissolved in alcohol (see addendum). The method was soon adopted by others. I had intended that the method would be used by office-based physicians who would prepare the carbowax fixative themselves but it soon became evident that they preferred to purchase the fixative from a commercial source. The reason became apparent—it was more practical and more economical to prepare the fixative in bulk than in the small quantities needed by individual users. This is due to the fact that only small amounts of the wax are needed and the laborious task of digging out small chunks, weighing this out on scales that might not be available and storing the rest of the remaining wax, added to the fact that small purchases of the wax commanded a premium price, made self-preparation of the carbowax fixative impractical. It occurred to me that this problem could be solved by packaging small, preweighed quantities of carbowax PEG 1450 or any of the other solid carbowaxes at low cost for use by the office-based physician. All he had to do was to add the packaged wax to any of the alcohols in his laboratory.

MANUFACTURING THE CARBOWAX STICK

Carbowax is a tradename for solid and liquid polyethylene glycols of the general formula $HOCH_2(CH_2OCH_2)_xCH_2OH$ and includes the following various solid polyethylene glycols: Carbowax 1000, Carbowax 1500, Carbowax PEG 1450, Carbowax 4000, and Carbowax 6000. Descriptions of these various carbowaxes can be found in a booklet dated 1962 published by the Union Carbide Corporation and also in The Merck Index published by Merck & Co., Inc. in 1968, page 210. Short descriptions of the above carbowaxes as listed in The Merck Index are as follows: Carbowax 1000 has an average molecular weight of 950–1050; it is a soft, white, waxy solid with a solidifying range of 35°–40° C. Carbowax 1500 has an average molecular weight of 500–600; it is a soft, white, waxy solid having the consistency of low-melting petroleum with a solidifying range of 35°–40° C. Carbowax PEG 1450 has an average molecular weight of 1300–1600; it is a soft, white, waxy solid with a solidifying range of 40°–50°. Carbowax 4000 has an average molecular weight of 3000–3700; it is a hard, white, waxy solid with a solidifying range of 50°–55° C. Carbowax 6000 has an average molecular weight of 6000–7500; it is a hard, white, waxy solid with a solidifying range of 50°–62° C.

Figure 2:
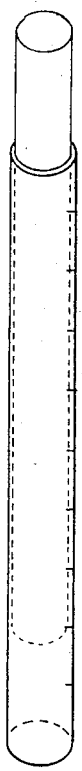
Figure 3:
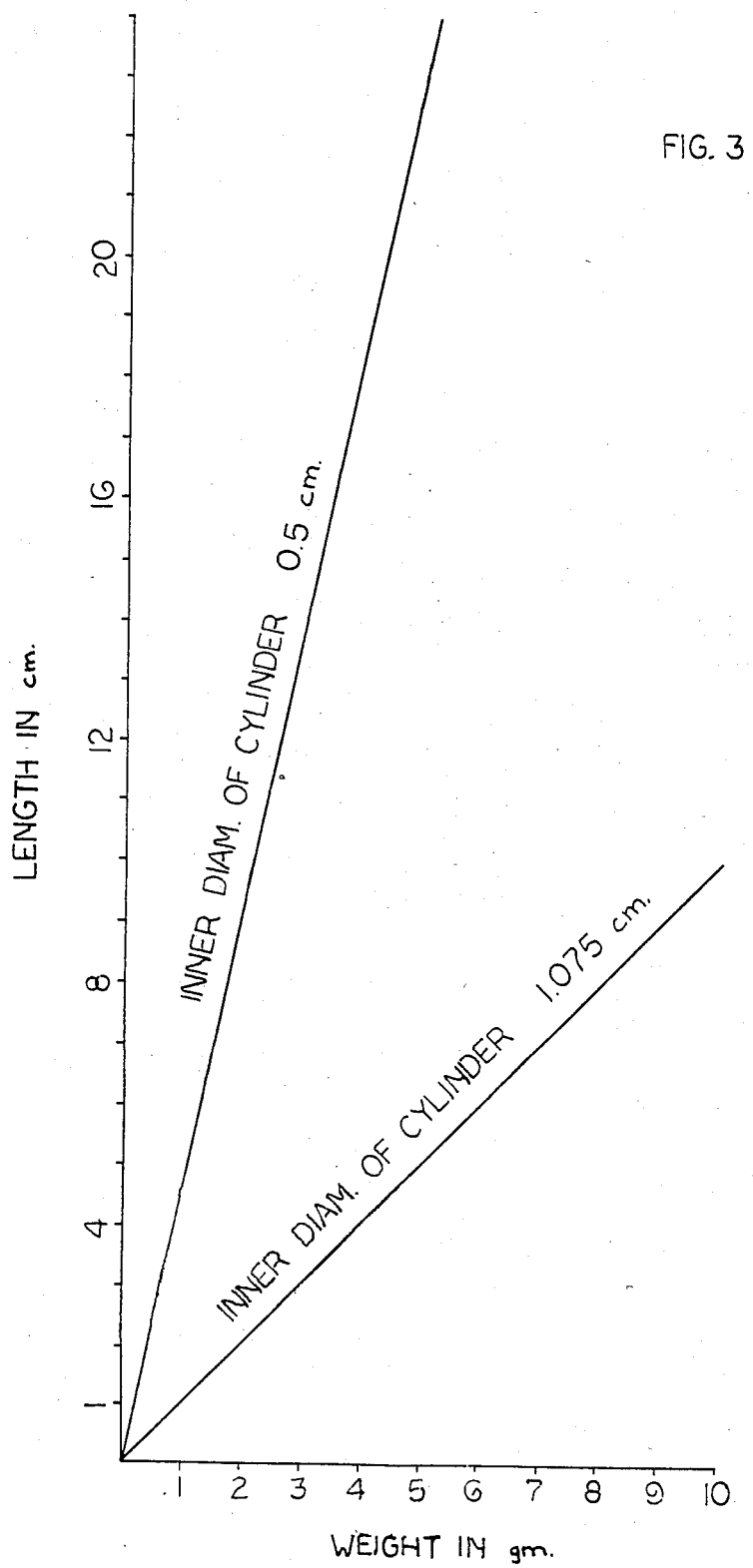

Carbowax PEG 1450 melts at 40°–50° C. It is formless but like any wax it can be molded. When poured on glass or metal surfaces it sticks on hardening. It does not stick to polyethylene surfaces. I purchased long, meter lengths of thin (0.25 mm), polyethylene tubes with a diameter of 0.5 cm. sealed one end and filled them with molten carbowax PEG 1450. The wax was allowed to cool and set. I now had a cylinder made up of polyethylene walls filled with solid carbowax PEG 1450. I had calculated that such a cylinder measuring 23.12 cm. in length would contain 5 gms. of carbowax PEG 1450 and that it could be subdivided into 5 equal parts each measuring 4.62 cm. in length each such section containing 1 gm. of carbowax PEG 1450 FIGS. 1 and 2. This relationship could be plotted on a graph so that intermediate weights could be determined from the graph FIG. 3. The sectioning was done with a sharp razor blade. The wax was extruded from its mold by pushing it out with any small blunt instrument. The wax did not adhere to the mold surface and no lubricant was necessary. It takes about 30 minutes for the wax stick to dissolve in alcohol. This can be hastened by breaking the stick into smaller pieces.

In todays usage the concentration of carbowax PEG 1450 varies from 2–10%. Minor variations are not critical. The type of delivery system used determines what concentration is most useful. The important thing is that enough wax remains on the slide after the alcohol evaporates to penetrate the cells and coat the slide so that the cells are not dehydrated. The desired weight is quickly calculated from the graph (see addendum) FIG. 2.

There are three delivery systems available to the user:
1. Using a dropper, flood the smear with the fixative and allow to dry.
2. Attach a 20 cc. test tube to a hand activated spray pump. Adding 1 gm. of carbowax PEG 1450 to the alcohol in the reservoir forms a 5% solution. This delivery system is free of ozone layer destroying FREON. It is also reusable so that there is nothing to discard.
3. Use the entire wax stick to make up 100 cc. of the fixative for use in Coplin jars or small capped bottles.

The advantages are many:
1. Low cost.
2. The wax sticks are easily stored for future use.
3. The molded wax is protected from warping and hygroscopic changes by the thin polyethylene mould form which is only removed prior to using the wax.
4. The desired weight is calculated from the table or graph and does not require scraping out and weighing small quantities of wax from a larger source.
5. None of the delivery systems pollute the atmosphere.
6. There is nothing to discard except the non-reusable polyethylene mold.

SUMMARY

My invention consists of manufacturing molded carbowax PEG 1450 sticks of constant size and weight. The weight of smaller units of the stick can be calculated from markings stamped on the surface of the polyethylene mold, or from a graph or conversion table which are supplied with the molded stick. The entire stick or its subunits are used in the preparation of small volumes of the carbowax PEG 1450 fixative now used in cancer cytology for fixing, protecting, mailing and conserving cytological smears, for example Papanicolaou smears in the study of cancer of the female cervix.

This supplies the solo physician, at low cost, the essential ingredient of the now universally used fixative in cancer cytology. He can now prepare his own fixative using his own alcohol rather than purchase at high cost those that are commercially available. The same method of manufacture can be applied to any of the other carbowaxes, for example 1000, 1500, 4000, 6000 or combinations of these with carbowax PEG 1450.

We claim:

1. A molded stick of synthetic wax comprising a cylindrical, hollow, plastic tube filled with a wax, polyethylene glycol, of the general formula $HOCH_2(CH_2OCH_2)_xCH_2OH$, the two of which when thus combined function synergistically as a single unit to provide a source of measured quantities of wax whose weight can be calculated from linear measurements stamped on the surface of the tube-mold.

2. The molded stick according to claim 1 wherein said synthetic wax is polyethylene glycol 1000 with an average molecular weight between 950–1050.

3. The molded stick according to claim 1 wherein the said synthetic wax is polyethylene glycol 1450 with an average molecular weight between 1300–1600.

4. A molded stick according to claim 1 wherein the said synthetic wax is a combination of polyethylene glycol 1000 and 1450.

5. The molded stick according to claim 1 wherein said plastic tubemold is made of semi-rigid, solid polyethylene of the general formula $[CH_2-CH_2]n$ said tube having flat tubular ends, a wall thickness of 0.05 centimeters and graduated centimeter or inch markings stamped on said surface.

6. The molded stick according to claim 5 wherein said tube has a inner diameter of of 0.5 centimeters and a length of 23.12 cm. centimeters and is filled with 5 grams of said wax.

7. The molded stick according to claim 5 wherein said tube has an inner diameter of 1.0 centimeters, a length of 10 centimeters and is filled with 10 grams of said wax.

* * * * *